United States Patent
Choi et al.

(10) Patent No.: US 9,763,994 B2
(45) Date of Patent: Sep. 19, 2017

(54) COMPOSITION FOR PROMOTING WOUND HEALING

(71) Applicant: INDUSTRY-ACADEMIC COOPERATION FOUNDATION, YONSEI UNIVERSITY, Seoul (KR)

(72) Inventors: Kang-Yell Choi, Seoul (KR); Soung-Hoon Lee, Seoul (KR); Hyun-Yi Kim, Seoul (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 4 days.

(21) Appl. No.: 14/567,268

(22) Filed: Dec. 11, 2014

(65) Prior Publication Data

US 2015/0224167 A1    Aug. 13, 2015

(30) Foreign Application Priority Data

Feb. 12, 2014  (KR) .................. 10-2014-0015791

(51) Int. Cl.

| A61K 38/10 | (2006.01) |
|---|---|
| A61K 38/16 | (2006.01) |
| A61K 45/06 | (2006.01) |
| A61K 31/19 | (2006.01) |
| A61K 38/17 | (2006.01) |

(52) U.S. Cl.
CPC .......... *A61K 38/10* (2013.01); *A61K 31/19* (2013.01); *A61K 38/16* (2013.01); *A61K 38/17* (2013.01); *A61K 45/06* (2013.01); *C07K 2319/00* (2013.01); *C07K 2319/10* (2013.01)

(58) Field of Classification Search
CPC ............. A61K 38/10; A61K 38/1709; A61K 47/48246; C07K 14/4703; C07K 2319/10; C07K 7/08
See application file for complete search history.

(56) References Cited

U.S. PATENT DOCUMENTS 9,150,630 B2 * 10/2015 Choi .................. C07K 14/4703
2011/0135652 A1   6/2011 Choi et al.

FOREIGN PATENT DOCUMENTS

| KR | 1012780730000 | 6/2013 |
|---|---|---|
| WO | 2009/151337 | 12/2009 |
| WO | 2014/073919 | 5/2014 |

OTHER PUBLICATIONS

Fathke et al. Wnt signaling induces epithelial differentiation during cutaneous wound healing. BMC Cell Biol. Jan. 20, 2006;7:4.*
Gurvich et al. Lithium and valproic acid: parallels and contrasts in diverse signaling contexts. Pharmacology & Therapeutics 96 (2002) 45-66.*
Kim, Hyun-Yi, et al., "CXXC5 is a transcriptional activator of Flk-1 and mediates bone morphogenic protein-induced endothelial cell differentiation and vessel formation," The FASEB Journal, Feb. 2014, vol. 28, pp. 1-12.
Lee, Soung-Hoon, et al., "Valproic Acid Induces Cutaneous Wound Healing In Vivo and Enhances Keratinocyte Motility," PLOS ONE, Nov. 2012, vol. 7, issue 11, pp. 1-10.
Zhang, D.L., et al., "Effect of Wnt signaling pathway on wound healing," Biochemical and Biophysical Research Communications, 2009, vol. 378, pp. 149-151.

* cited by examiner

*Primary Examiner* — Satyanarayana R Gudibande
*Assistant Examiner* — Jia-Hai Lee
(74) *Attorney, Agent, or Firm* — Duane Morris LLP; J. Rodman Steele, Jr.; Gregory M. Lefkowitz

(57) ABSTRACT

The present disclosure relates to a composition for promoting wound healing that may be used as a pharmaceutical composition, or a cosmetic composition for promoting wound healing, which contains a polypeptide including an amino acid sequence of SEQ ID NO 1. The composition may be usefully used for a wound care drug or a functional cosmetic product for wound care.

12 Claims, 5 Drawing Sheets

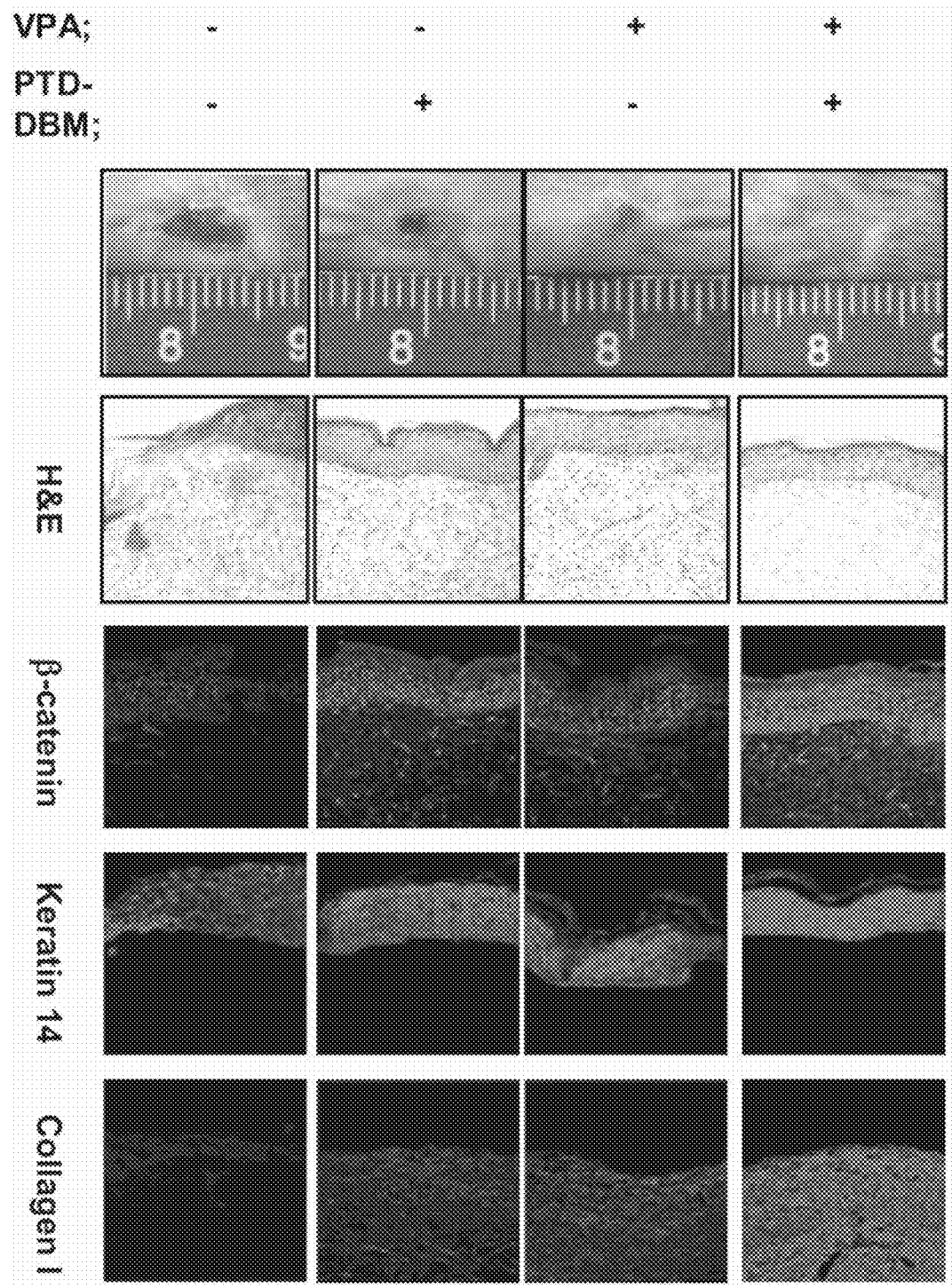

SEQUENCE LISTING

```
<160> NUMBER OF SEQ ID NOS: 10

<210> SEQ ID NO 1
<211> LENGTH: 13
<212> TYPE: PRT
<213> ORGANISM: Unknown
<220> FEATURE:
<223> OTHER INFORMATION: Description of Unknown: Dvl minimal binding
      peptide

<400> SEQUENCE: 1

Arg Lys Thr Gly His Gln Ile Cys Lys Phe Arg Lys Cys
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Arg Arg Arg Arg Arg Arg
```

```
1               5

<210> SEQ ID NO 3
<211> LENGTH: 11
<212> TYPE: PRT
<213> ORGANISM: Human immunodeficiency virus

<400> SEQUENCE: 3

Tyr Gly Arg Lys Lys Arg Arg Gln Arg Arg Arg
1               5                   10

<210> SEQ ID NO 4
<211> LENGTH: 34
<212> TYPE: PRT
<213> ORGANISM: Herpes simplex virus

<400> SEQUENCE: 4

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 5
<211> LENGTH: 16
<212> TYPE: PRT
<213> ORGANISM: Drosophila sp.

<400> SEQUENCE: 5

Arg Gln Ile Lys Ile Trp Phe Gln Asn Arg Arg Met Lys Trp Lys Lys
1               5                   10                  15

<210> SEQ ID NO 6
<211> LENGTH: 21
<212> TYPE: PRT
<213> ORGANISM: Unknown
<220> FEATURE:
<223> OTHER INFORMATION: Description of Unknown: Transportan
      peptide

<400> SEQUENCE: 6

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 7
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Arg Arg Arg Arg Arg Arg Arg Gly Gly Gly Gly Arg Lys Thr Gly
1               5                   10                  15

His Gln Ile Cys Lys Phe Arg Lys Cys
            20                  25

<210> SEQ ID NO 8
<211> LENGTH: 8
<212> TYPE: PRT
<213> ORGANISM: Artificial Sequence
```

```
-continued

<220> FEATURE:
<223> OTHER INFORMATION: Description of Artificial Sequence: Synthetic
      peptide
<220> FEATURE:
<221> NAME/KEY: misc_feature
<222> LOCATION: (1)..(8)
<223> OTHER INFORMATION: This sequence may encompass 4 to 8 residues

<400> SEQUENCE: 8

Gly Gly Gly Gly Gly Gly Gly Gly
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly
1

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Arg Arg Arg Arg Arg Arg Arg Gly Gly Gly Gly Arg Lys Thr Gly
1               5                   10                  15

His Gln Ile Cys Lys Phe Arg Lys Cys Lys
            20                  25
```

COMPOSITION FOR PROMOTING WOUND HEALING

CROSS-REFERENCE TO RELATED APPLICATIONS

This application claims priority under 35 U.S.C. §119 to Korean Patent Application No. 10-2014-0015791 filed on Feb. 12, 2014 in the Korean Intellectual Property Office, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 23, 2015, is named G1035-04201_SL.txt and is 3,054 bytes in size.

TECHNICAL FIELD

The present disclosure relates to a composition for promoting wound healing that may be used as a pharmaceutical composition, a quasi-drug composition or a cosmetic composition for promoting wound healing.

BACKGROUND

The human skin performs many functions. The most important function is the barrier function of protecting the body from outside. A wound is a state where the normal structure of the skin that performs the barrier function is damaged. If the skin is damaged, the wound site may be invaded by pathogens as it is exposed to outside. Accordingly, quick wound healing is necessary to prevent further infection and excessive inflammation resulting therefrom. Excessive inflammation not only slows wound healing but also leaves scars.

Wound healing refers complete suture of the skin clinically. General wound except chronic wound heals completely approximately in 3-14 days. Wound healing is a complicated process wherein various types of cells such as keratinocytes, fibroblasts, endothelial cells, macrophages, platelets, etc, interact with each other.

At present, Dongkook Pharmaceutical's 'Madecassol' (marketed since 1985) and Dong Wha Pharm's 'Fucidin' (marketed since 1980) are available as wound care drugs in Korea. The two drugs are generally similar in efficacy, but Fucidin has a better advantage in antibacterial activity and Madecassol has a better advantage in reducing scars.

Although the existing steroid ointment is effective in reducing inflammation, suppressing immunity and treating allergic diseases, it may cause unwanted pockmarks, skin wrinkles, folliculitis, etc. and is ineffective for fungal diseases such as athlete's foot. Meanwhile, an antibiotic-containing ointment has the resistance problem and may cause many side effects when used for wound on children's soft skin. Thus, wound care drugs based on the wound healing mechanism are entering the Korean market to overcome the limitations of the steroid and antibiotic ointments. Also, injuries more severe than minor skin wounds, deep wounds occurring after surgery of skin diseases such as melanoma, wounds associated with other diseases such as diabetes, or the like require longer time for healing and often leave scars. Daewoong Pharmaceutical marketed a wound care drug 'Easyef ointment' containing the epidermal growth factor (EGF) as an over-the-counter drug for the first time in Korea. The epidermal growth factor helps to prevent scar formation by promoting covering of the wound site (re-epithelialization) and formation of proud flesh (proliferation of granulation tissue). However, the epidermal growth factor protein costs a lot of costs and efforts for production.

SUMMARY

The present disclosure is directed to providing a composition for promoting wound healing, containing a peptide including a part of an amino acid sequence of the protein CXXC4 or CXXC5 existing in the body, which is a safe peptide that is free from rejection or side effects on administration and is degraded naturally with time, that can be used for pharmaceutical or cosmetic purposes.

In an aspect, the present disclosure provides a pharmaceutical composition or a cosmetic composition for promoting wound healing, containing a polypeptide including an amino acid sequence of SEQ ID NO 1.

In an exemplary embodiment of the present disclosure, the polypeptide may further include an amino acid sequence encoding a protein transduction domain (PTD) inserted to the amino acid sequence of SEQ ID NO 1 and the protein transduction domain (PTD) may be poly $R_8$ (SEQ ID NO: 2), HIV-Tat, HSV VP22, Antp or transportan.

In an exemplary embodiment of the present disclosure, the polypeptide may further include a linker inserted between the amino acid sequence of SEQ ID NO 1 and the amino acid sequence encoding a PTD, which provides mobility to the functional peptide.

In an exemplary embodiment of the present disclosure, the composition may further contain a Wnt ligand or a low-molecular-weight compound which activates the Wnt signal transduction pathway in order to maximize wound healing effect, such as valproic acid (VPA), indirubin derivatives such as 6-bromoindirubin-3'-oxime (BIO), 6-bromoindirubin acetoxime (BIA), indirubin 3'-oxime (IO), etc., lithium chloride (LiCl), etc.

The composition containing a polypeptide including an amino acid sequence of SEQ ID NO 1 according to the present disclosure can promote wound healing and may be usefully used as a pharmaceutical composition or a cosmetic composition. Accordingly, it can be used for a wound care drug or a wound care cosmetic product.

BRIEF DESCRIPTION OF DRAWINGS

FIG. 2A shows a result showing that PTD-DBM according to the present disclosure can effectively heal acute wound in a mouse model.

DETAILED DESCRIPTION OF EMBODIMENTS

Hereinafter, the present disclosure is described in detail.

The present disclosure relates to a composition for promoting wound healing, containing a polypeptide including an amino acid sequence of SEQ ID NO 1.

```
[SEQ ID NO 1]: RKTGHQICKFRKC
```

The amino acid sequence of SEQ ID NO 1 corresponds to a DBM (Dvl minimal binding) peptide which is a part of the protein CXXC4 or CXXC5 existing in the body. The DBM peptide inhibits interaction between Idbf (inhibitor of Dvl and bone formation, CXXC5) and Dvl (dishevelled), thereby activating the Wnt/β-catenin signal transduction pathway.

As demonstrated in the following examples and figures, application of the polypeptide having an amino acid sequence of SEQ ID NO 1 with 8 arginine residues (SEQ ID NO: 2) attached to the N-terminal to a mouse acute wound leads to quick re-epithelialization of the mouse wound and increase in wound healing markers such as β-catenin, keratin 14, collagen I, etc.

Accordingly, the polypeptide including an amino acid sequence of SEQ ID NO 1 according to the present disclosure may be used as a pharmaceutical composition, a cosmetic composition, etc. for promoting wound healing.

The polypeptide according to the present disclosure may further include an amino acid sequence encoding a protein transduction domain (PTD) inserted to the amino acid sequence of SEQ ID NO 1, so as to induce infiltration of the peptide having an amino acid sequence of SEQ ID NO 1 (DBM) into a cell through a cell membrane.

The PTD usually consists of a basic amino acid such as arginine, lysine, etc. By inserting the PTD at the N-terminal or C-terminal of the amino acid sequence of SEQ ID NO 1, infiltration into a cell through a cell membrane may be induced.

In an exemplary embodiment, the PTD may be poly $R_8$ (SEQ ID NO: 2), HIV-Tat, HSV VP22, Antp or transportan. The poly $R_8$ (SEQ ID NO: 2) may have an amino acid sequence of SEQ ID NO 2, the HIV-Tat may have an amino acid sequence of SEQ ID NO 3, the HSV VP22 may have an amino acid sequence of SEQ ID NO 4, the Antp may have an amino acid sequence of SEQ ID NO 5, and the transportan may have an amino acid sequence of SEQ ID NO 6.

```
[SEQ ID NO 2]: RRRRRRRR

[SEQ ID NO 3]: YGRKKRRQRRR

[SEQ ID NO 4]: DAATATRGRSAASRPTERPRAPARSASRPRRPVE

[SEQ ID NO 5]: RQIKIWFQNRRMKWKK

[SEQ ID NO 6]: AGYLLGKINLKALAALAKKIL
```

The polypeptide according to the present disclosure may further include a linker inserted between the amino acid sequence of SEQ ID NO 1 and the amino acid sequence encoding a PTD. In an exemplary embodiment, the linker inserted between the amino acid sequence of SEQ ID NO 1 and the amino acid sequence encoding a PTD may consist of 4-12 amino acids, specifically 4-8 glycines (SEQ ID NO: 8), and the polypeptide according to the present disclosure further having the linker inserted may have an amino acid sequence of SEQ ID NO 7.

```
[SEQ ID NO 7]: RRRRRRRRGGGGRKTGHQICKFRKC
```

Figure 1:
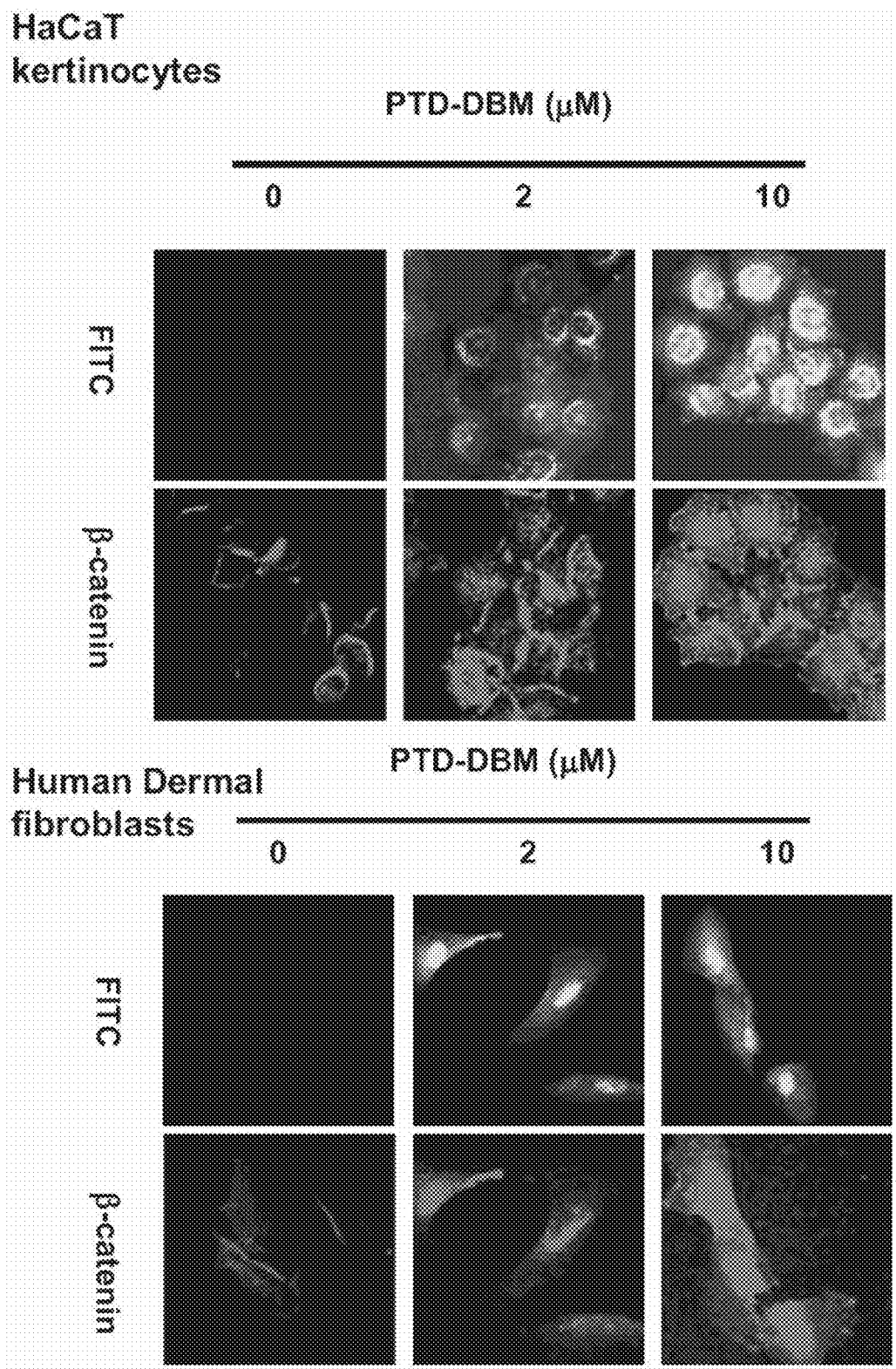
FIG. 1 shows a result of immunocytochemical staining after treating keratinocytes and fibroblasts with a composition for promoting wound healing according to the present disclosure.

As seen from FIG. 1, when keratinocytes and fibroblasts which play an important role in wound healing were treated with a composition containing the polypeptide according to the present disclosure, it was confirmed that the peptide infiltrated into the cells well and increased β-catenin in a concentration-dependent manner.

In particular, the keratinocytes found in the epidermis constitute the basal layer of the skin and form the horny layer (stratum corneum) through structural expansion and modification. The speed of wound healing is affected by the proliferation and migration speed of keratinocytes among other factors. It can be seen that the polypeptide according to the present disclosure is effective in wound healing since it infiltrates well into keratinocytes and increases β-catenin.

The composition for promoting wound healing according to the present disclosure may further contain a Wnt ligand or a low-molecular-weight compound which activates the Wnt signal transduction pathway in order to maximize wound healing effect. For example, it may further contain valproic acid (VPA), indirubin derivatives such as 6-bromoindirubin-3'-oxime (BIO), 6-bromoindirubin acetoxime (BIA) and indirubin 3'-oxime (IO), lithium chloride (LiCl), etc. As demonstrated in the following examples and figures, the Wnt ligand or low-molecular-weight compound accelerates re-epithelialization of acute wound and leads to increase in wound healing markers.

The composition for promoting wound healing according to the present disclosure may be prepared into a formulation that can be administered to the skin wound through direct application, spraying, etc. For example, it may be prepared as cream, lotion, ointment, aerosol, gel or pack. The ingredients suitable for each formulation or a method for preparing the same are well known in the art. Those skilled in the art can adequately select the Ingredients commonly used to prepare formulations for external application to prepare the formulation.

Examples of such ingredients for ointment, cream, gel and lotion formulations include bases such as white vaseline, yellow vaseline, lanolin, white beeswax, cetanol, stearyl alcohol, stearic acid, hydrogenated oil, hydrocarbon gel, polyethylene glycol, liquid paraffin, squalane, etc. solvents and solubilizing agents such as oleic acid, isopropyl myristate, glyceryl triisooctanoate, crotamiton, diethyl sebacate, diisopropyl adipate, hexyl laurate, fatty acid, fatty acid ester, aliphatic alcohol, vegetable oil, etc., antioxidants such as tocopherol derivative, L-ascorbic acid, dibutylhydroxytoluene, butylhydroxyanisole, etc., antiseptics such as p-hydroxybenzoate, etc., moisturizers such as glycerin, propylene glycol, sodium hyaluronate, etc., surfactants such as polyoxyethylene derivatives, glycerin fatty acid ester, sucrose fatty acid ester, sorbitan fatty acid ester, propylene glycol fatty acid ester, lecithin, etc., thickeners such as carboxyvinyl polymer, xanthan gum, carboxymethyl cellulose, sodium carboxymethyl cellulose, hydroxypropyl cellulose, hydroxypropyl methylcellulose, etc., and so forth.

For aerosol, in addition to the ingredients used for the preparation of ointment, cream, gel, suspension, emulsion, liquid, lotion, etc., various stabilizers, buffers, correctives, suspending agents, emulsifiers, flavoring agents, preservatives, solubilizing agents and other suitable additives may be added.

The composition for promoting wound healing according to the present disclosure may be a pharmaceutical composition, a quasi-drug composition or a cosmetic composition.

When the composition of the present disclosure is a pharmaceutical composition, it may be administered parenterally or topically through topical application. An adequate administration dose of the pharmaceutical composition may vary depending on the patient's condition and body weight, degree of wound, type of the composition, route and period of administration, etc. and may be selected adequately by those skilled in the art.

In particular, when the pharmaceutical composition of the present disclosure is prepared as liquid, cream, lotion, gel or aerosol for topical application, it may contain commonly used suitable additives, e.g., preservatives, solvents aiding the infiltration of the composition, softeners in case of ointment or cream, or the like. The formulation for topical application may further contain a commonly used carrier, e.g., a cream or ointment base or ethanol or oleyl alcohol for lotion. The carrier may account for from about 1% to about 98%, more generally up to about 80%, of the formulation.

When the composition of the present disclosure is a cosmetic composition, it may be prepared into various formulations. For example, it may be prepared into emulsion (oil-in-water, water-in-oil or multi-phase), lotion, cream, solution, suspension (anhydrous or aqueous), anhydrous product (oil or glycol), gel, mask, pack, powder, etc.

The cosmetic composition of the present disclosure may further contain a cosmetically acceptable carrier. As used herein, the "cosmetically acceptable carrier" refers to a known compound or composition used in cosmetic formulations or a compound or composition to be developed, which is free from toxicity, instability or irritability upon contact with the skin, so that it can be used for human.

The cosmetic composition of the present disclosure may contain the carrier in an amount of about 1-99.99 wt %, specifically about 90-99.99 wt %, based on the total weight of the composition. However, since the content may vary depending on the formulation of the cosmetic composition of the present disclosure, the part to which it is applied (e.g., face, neck, etc.) or the desired application amount, the above-described range should not be construed as limiting the scope of the present disclosure by any means.

Examples of the carrier may include alcohol, oil, surfactant, fatty acid, silicone oil, humectant, moisturizer, viscosity modifier, emulsifier, stabilizer, sunscreen, colorant, fragrance, etc. Compounds or compositions that may be used as the alcohol, oil, surfactant, fatty acid, silicone oil, humectant, moisturizer, viscosity modifier, emulsion, stabilizer, sunscreen, colorant, fragrance, etc. are known in the art and may be adequately selected by those skilled in the art.

EXAMPLES

Hereinafter, the present disclosure will be described in more detail through specific examples. However, the following examples are for illustrative purposes only and it will be apparent to those of ordinary skill in the art that the scope of the present disclosure is not limited by the examples.

Example 1

In order to confirm the effect of a polypeptide including an amino acid sequence of SEQ ID NO 1, a PolyR$_8$-DBM peptide wherein poly R$_8$ (RRRRRRRR) (SEQ ID NO: 2) and a polyglycine linker (GGGG) (SEQ ID NO: 9) are attached to the N-terminal of SEQ ID NO 1 and lysine and a fluorescent dye FITC (fluorescein isothiocyanate) are attached to the C-terminal was synthesized.

PolyR$_8$-DBM: RRRRRRRRGGGGRKTGHQICKFRKCK-(FITC)

Test Example 1

For immunocytochemical staining, keratinocytes or fibroblasts were cultured on a 24-well plate and fixed in 4% paraformaldehyde for 15 minutes. After treating with 0.1% Triton X-100 for 15 minutes so that antibodies can permeate well and blocking with albumin so as to prevent nonspecific antigen-antibody reactions, antigen-antibody reactions were induced by treating with β-catenin antibodies. Then, after inducing antigen-antibody reactions by treating with fluorescence-labeled secondary antibodies that can recognize the antibodies as antigens, the result was observed under a fluorescence microscope.

As seen from FIG. 1, when the two types of cells that play important roles in wound healing (keratinocytes and fibroblasts) were treated with the composition according to the present disclosure, the peptide synthesized in Example 1 could effectively infiltrate into the cells and increased β-catenin in a concentration-dependent manner.

Test Example 2

(A) In order to confirm the wound healing promoting effect of the peptide synthesized in Example 1, hair was removed the back of a 7-week-old C3H mouse and a 1.5 cm×1.5 cm sized wound was made. For a control group, 10 μL of a vehicle (50% ethanol, 20% propylene glycol, 30% water) was applied once a day for a period of 12 days. For test groups, 10 μL of the peptide or valproic acid (VPA) dissolved in the vehicle at concentrations of 100 μM and 500 mM, respectively, was applied. The skin tissue of the experimental mouse was fixed in 4% paraformaldehyde, embedded in paraffin and sliced with a thickness of 4 μm. The sliced tissue was deparaffinized, rehydrated and then stained with hematoxylin (violet) and eosin (pink) for observation of histological structure. For immunohistochemical staining, the skin tissue slice was deparaffinized, rehydrated and then incubated with 10 mM sodium citrate buffer at 121° C. for 15 minutes to recover antigenicity. The slice was blocked with albumin to prevent nonspecific antigen-antibody reactions and then antigen-antibody reactions were induced by treating with β-catenin (1:100), keratin 14 (1:1000) and collagen I (1:500) antibodies used as wound healing markers. Subsequently, after inducing antigen-antibody reactions by treating the slice with fluorescence-labeled secondary antibodies that can recognize the antibodies as antigens, the result was observed using a fluorescence microscope.

(B) In order to compare the wound healing promoting effect of the synthesized peptide with that of the existing drug, 10 μL of a vehicle (50% ethanol, 20% propylene glycol, 30% water), 100 μM PTD-DBM or 1.5 μM fibronectin was applied on a 1.5 cm×1.5 cm sized wound of a 7-week-old C3H mouse once a day for a period of 12 days.

Figure 2B:
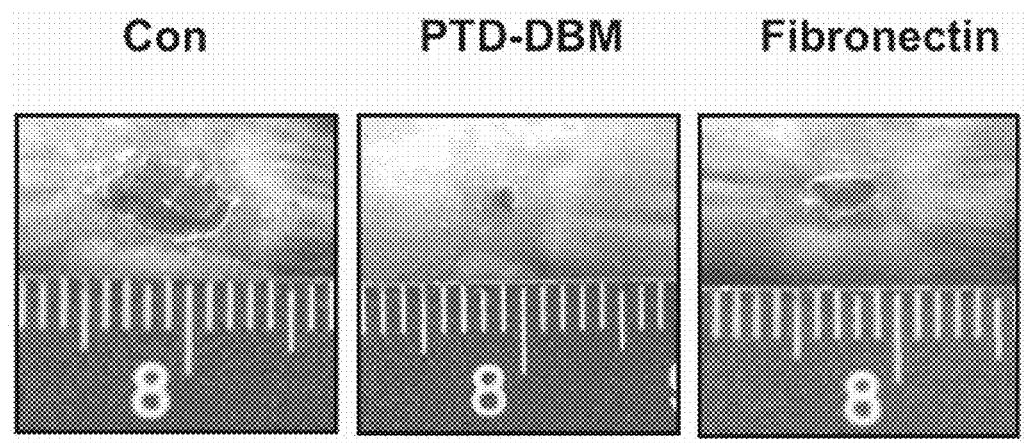
FIG. 2B shows a result of comparing the wound healing effect of PTD-DBM according to the present disclosure with that of fibronectin whose wound healing effect has been identified.

As seen from FIGS. 2A and 2B, the PTD-DBM according to the present disclosure could quickly heal the acute wound in the mouse model and the effect of the PTD-DBM according to the present disclosure was synergically improved when it was used in combination with valproic acid (VPA).

Also, the H&E (hematoxylin and eosin) staining image shows that the PTD-DBM according to the present disclosure and VPA led to quick re-epithelialization of the acute wound. A synergistic effect was also achieved when the PTD-DBM and VPA were treated together with the wound healing markers such as β-catenin, keratin 14, collagen I, etc.

The wound healing effect of the PTD-DBM was excellent when compared with that of fibronectin.

Test Example 3

The wound tissue used in Test Example 2 was lysed with RIPA buffer and proteins were isolated on 10% SDS polyacrylamide gel and then transferred onto a membrane. The membrane was blocked using 5% nonfat dry skim milk and then incubated with β-catenin (1:1000), α-SMA (1:1000), keratin 14 (1:1000) and collagen I (1:2000) antibodies. After inducing antigen-antibody reactions by adding enzyme-conjugated secondary antibodies that can recognize the antibodies as antigens, the result was observed using a LAS image analyzer.

Figure 3:
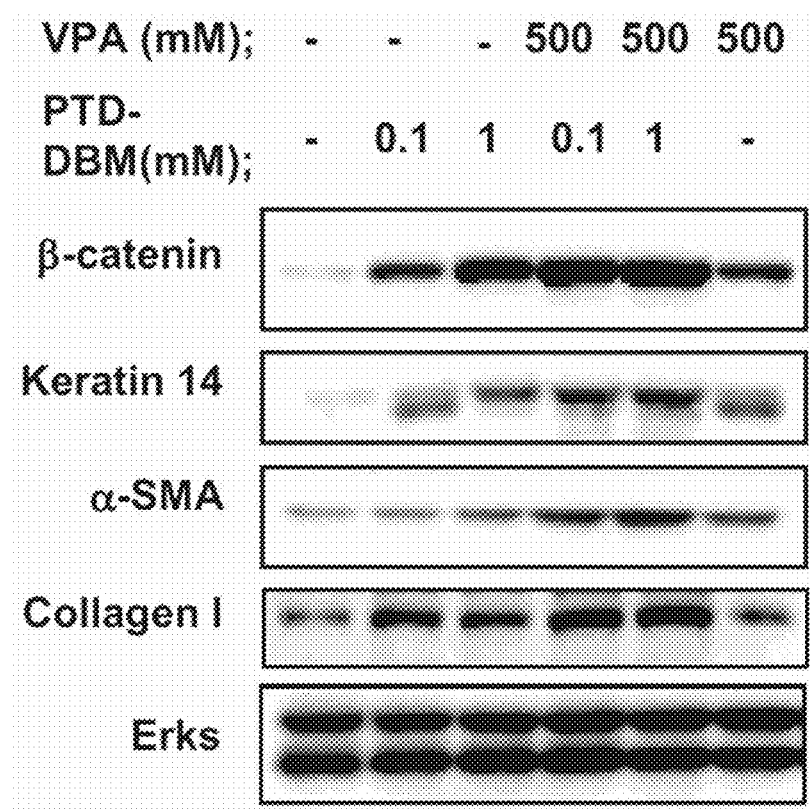
FIG. 3 shows a result of western blotting of a mouse wound treated with a composition for promoting wound healing according to the present disclosure.

As seen from FIG. 3, the western blotting result of the mouse acute wound treated with the PTD-DBM according to the present disclosure and VPA revealed that the wound healing markers such as β-catenin, keratin 14, α-SMA or collagen I were increased as compared to the control and the wound healing markers increased synergistically when the wound was treated with the PTD-DBM and VPA together.

Test Example 4

(A) The mouse tissue used in Test Example 2 was fixed in 4% paraformaldehyde, embedded in paraffin and sliced with a thickness of 4 µm. The sliced tissue was deparaffinized, rehydrated and then subjected to van Gieson staining, Masson's trichrome staining and picrosirius red staining in order to evaluate the degree of collagen synthesis. Van Gieson staining was conducted by immersing the slide in Weigert's solution for 10 minutes and then in picro fuchsin solution for 2 minutes. Masson's trichrome staining was conducted by immersing the slide in Weigert's iron hematoxylin solution for 10 minutes and then in Biebrich scarlet/acid fuchsin and aniline blue for 5 minutes, respectively. Picrosirius red staining was conducted by immersing the slide in Weigert's solution for 8 minutes and then in picrosirius red for 1 hour.

(B) The tissue used in Test Example 2 was dried in an incubator at 60° C. and then hydrolyzed at 110° C. with 6 N HCl. After adding chloramine T and Ehrlich's reagent to the hydrolyzed tissue, absorbance was measured at 550 nm using the FLUOstar OPTIMA luminometer.

Figure 4A:
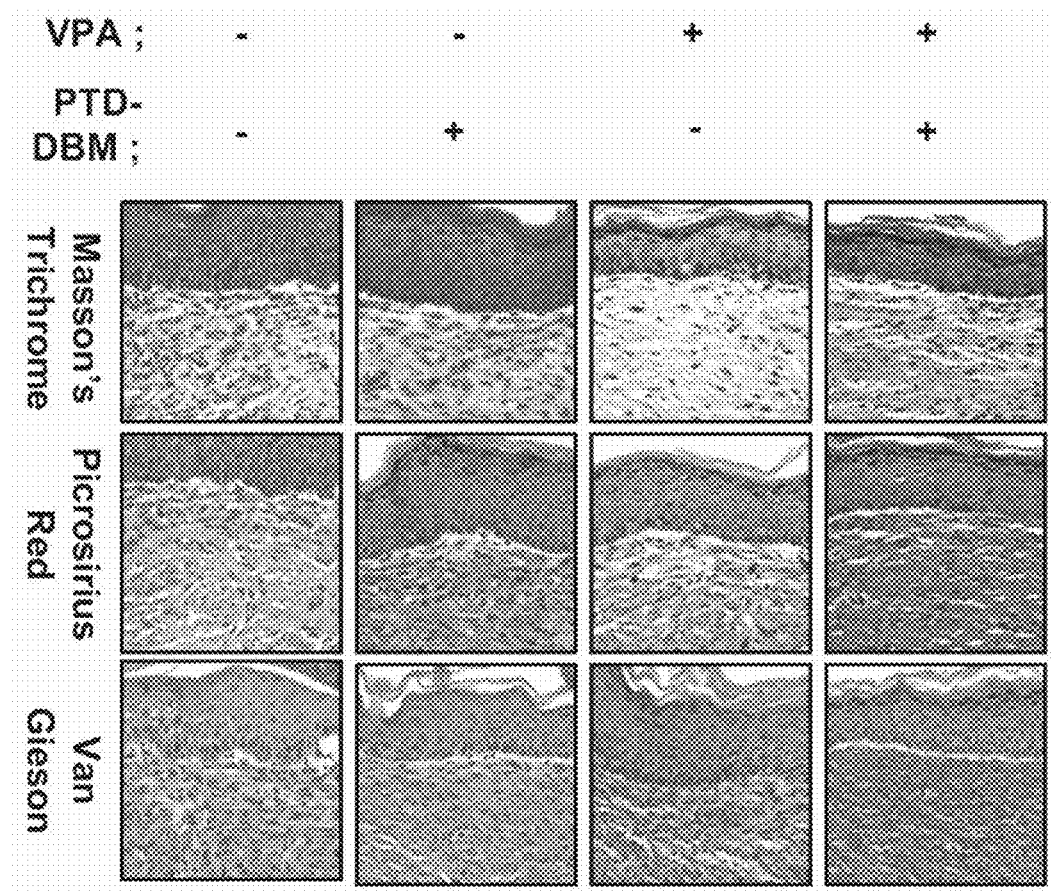
FIG. 4A shows a result of Masson's trichrome staining, picrosirius red staining and van Gieson staining of a mouse acute wound tissue treated with a composition for promoting wound healing according to the present disclosure.
Figure 4B:
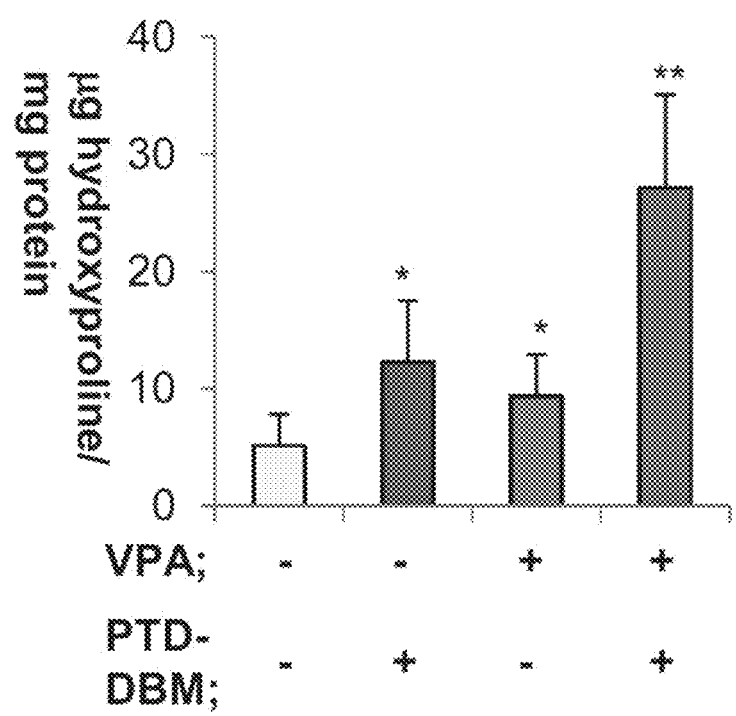
FIG. 4B shows a result of hydroxproline assay for quantitative measurement of collagen in a mouse acute wound tissue treated with a composition for promoting wound healing according to the present disclosure.

As seen from FIGS. 4A and 4B, increased collagen in the acute wound tissue treated with the PTD-DBM according to the present disclosure and VPA was confirmed by Masson's trichrome staining, picrosirius red staining and van Gieson staining. There was a synergistic effect in the increase of collagen synthesis when the wound was treated with the PTD-DBM and VPA together. This result was confirmed again by hydroxproline assay, which quantitatively measures collagen.

SEQUENCE LIST PRETEXT

[SEQ ID NO 1]: RKTGHQICKFRKC

[SEQ ID NO 2]: RRRRRRRR

[SEQ ID NO 3]: YGRKKRRQRRR

[SEQ ID NO 4]: DAATATRGRSAASRPTERPRAPARSASRPRRPVE

[SEQ ID NO 5]: RQIKIWFQNRRMKWKK

[SEQ ID NO 6]: AGYLLGKINLKALAALAKKIL

[SEQ ID NO 7]: RRRRRRRGGGGRKTGHQICKFRKC

What is claimed is:

1. A method of treating a skin wound of a subject in need thereof, comprising administering a composition topically to a skin wound, wherein the composition comprises (i) a polypeptide comprising an amino acid sequence of SEQ ID NO 1 and (ii) an activator of the Wnt signal transduction pathway is selected from the group consisting of valproic acid (VPA), 6-bromoindirubin-3'-oxime (BIO), 6-bromoindirubin acetoxime (BIA), indirubin 3'-oxime (IO), and lithium chloride (LiCl).

2. The method according to claim 1, wherein the polypeptide further comprises an amino acid sequence encoding a protein transduction domain (PTD) inserted to the amino acid sequence of SEQ ID NO 1.

3. The method according to claim 2, wherein the protein transduction domain (PTD) comprises poly $R_8$, HIV-Tat, HSV VP22, Antp or transportan.

4. The method according to claim 2, wherein the polypeptide further comprises a linker inserted between the amino acid sequence of SEQ ID NO 1 and the amino acid sequence encoding a PTD.

5. The method according to claim 1, wherein the method comprises accelerating healing of the skin wound.

6. The method according to claim 1, wherein the activator of the Wnt signal transduction pathway is valproic acid.

7. The method according to claim 6, wherein the polypeptide further comprises an amino acid sequence encoding a protein transduction domain (PTD) inserted to the amino acid sequence of SEQ ID NO 1.

8. The method according to claim 7, wherein the protein transduction domain (PTD) comprises poly $R_8$, HIV-Tat, HSV VP22, Antp or transportan.

9. The method according to claim 7, wherein the polypeptide further comprises a linker inserted between the amino acid sequence of SEQ ID NO 1 and the amino acid sequence encoding a PTD.

10. The method according to claim 6, wherein the method comprises accelerating healing of the skin wound.

11. The method according to claim 6, wherein the administering step comprises applying an ointment, a cream, a gel, a lotion, or an aerosol directly to the skin wound.

12. The method according to claim 1, wherein the administering step comprises applying an ointment, a cream, a gel, a lotion, or an aerosol directly to the skin wound.

* * * * *